US00PP22130P2

(12) United States Plant Patent
Probst

(10) Patent No.: US PP22,130 P2
(45) Date of Patent: Sep. 6, 2011

(54) ***COREOPSIS* PLANT NAMED 'LIMBO'**

(50) Latin Name: ***Coreopsis* hybrid**
Varietal Denomination: Limbo

(76) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 12/660,455

(22) Filed: Feb. 26, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — June Hwu
(74) *Attorney, Agent, or Firm* — Penny J. Aguirre

(57) ABSTRACT

A new cultivar of hybrid *Coreopsis* named 'Limbo' characterized its inflorescences with ray florets that are solid creamy white in color, its bushy and relatively short plant habit, its long blooming habit, its sterility, and its vigorous growth habit.

2 Drawing Sheets

Botanical classification: *Coreopsis* hybrid.
Variety denomination: 'Limbo'.

CROSS REFERENCE TO A RELATED APPLICATION

This application is co-pending with a U.S. Plant Patent application filed for a plant derived from similar parentage in the Inventor's breeding program that is entitled *Coreopsis* Plant Named 'Caliente' (U.S. Plant Pat. No. 21,869), *Coreopsis* Plant Named 'Salsa' (U.S. Plant patent application Ser. No. 12/660,464), *Coreopsis* Plant Named 'Cha Cha Cha' (U.S. Plant patent application Ser No. No. 12/660,480), *Coreopsis* Plant Named 'Mambo' (U.S. Plant patent application Ser. No. 12/660,454), *Coreopsis* Plant Named 'Jive' (U.S. Plant patent application Ser. No. 12/660,491).

BACKGROUND OF THE INVENTION

The present invention relates to a new and distinct cultivar of *Coreopsis* plant, botanically of hybrid origin and known as *Coreopsis* 'Limbo' and will be referred to hereinafter by its cultivar name, 'Limbo'. The new cultivar of *Coreopsis* is an herbaceous annual grown for use in borders and containers.

The new invention arose from an ongoing controlled breeding program in Hubbardston, Mass. The objective of the breeding program is to develop hybrid cultivars of *Coreopsis* with unique and superior garden attributes. The Inventor crossed *Coreopsis* 'Sweet Dreams' (U.S. Plant Pat. No. 12,720) and *Coreopsis rosea* with *Coreopsis tinctoria* and another annual type species that are not commercialized and made six generations of crosses to produce interspecific hybrids to utilize in his breeding work. The new variety was developed with a goal of producing new cultivars of *Coreopsis* with unique flower colorations, short and bushy plant habits, and sterility to lengthen bloom periods.

The Inventor made a controlled cross in August 2006 in his test garden in Hubbardston, Mass. between *Coreopsis* 'Sweet Dreams' as the female parent and an unnamed F6 generation seedling produced from crosses of unnamed hybrid *Coreopsis* from his breeding program and *Coreopsis rosea* as the male parent. 'Limbo' was selected in August 2007 as a single unique plant amongst the resulting seedlings.

Asexual reproduction of the new cultivar was first accomplished by stem cuttings in Kensington, Conn. in August of 2007 under the direction of the Inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Limbo' as unique from all *Coreopsis* cultivars and species known to the Inventor.

1. 'Limbo' exhibits composite inflorescences with ray florets that are solid creamy white in color.
2. 'Limbo' exhibits a bushy plant habit and is relatively short in height; reaching 16 to 24 inches (40.6 to 61 cm) in height.
3. 'Limbo' exhibits a vigorous growth habit.
4. 'Limbo' exhibits a long blooming period; blooming from June through August in Massachusetts.
5. 'Limbo' has been observed to be sterile.

The female parent, 'Sweet Dreams', differs from 'Limbo' in being taller in plant height (reaching up to 30 inches in height) and in having inflorescences with ray florets that are pink in color with a burgundy eye zone. The male parent differs from 'Limbo' in having a shorter blooming period (not sterile) and in having inflorescences with ray florets that are solid gold in color. 'Limbo' can be most closely compared to a cultivar from similar parentage, 'Jive'. 'Jive' is similar to 'Limbo' in plant habit and blooming habit. 'Jive' differs from 'Limbo' in being shorter in height (reaching 12 to 18 inches in height) and in having inflorescences with ray florets that are white in color with large eye zones that are dark burgundy-purple in color.

BRIEF DESCRIPTION OF THE DRAWING

The accompanying colored photographs illustrate the overall appearance and distinct characteristics of the new *Coreopsis*.

The photograph in FIG. 1 was taken in late summer of a five month-old plant of 'Limbo' as grown outdoors in a mixed container planting in New Hope, Minn. and shows the bushy plant habit and floriferous blooming habit of 'Limbo'.

Figure 1:
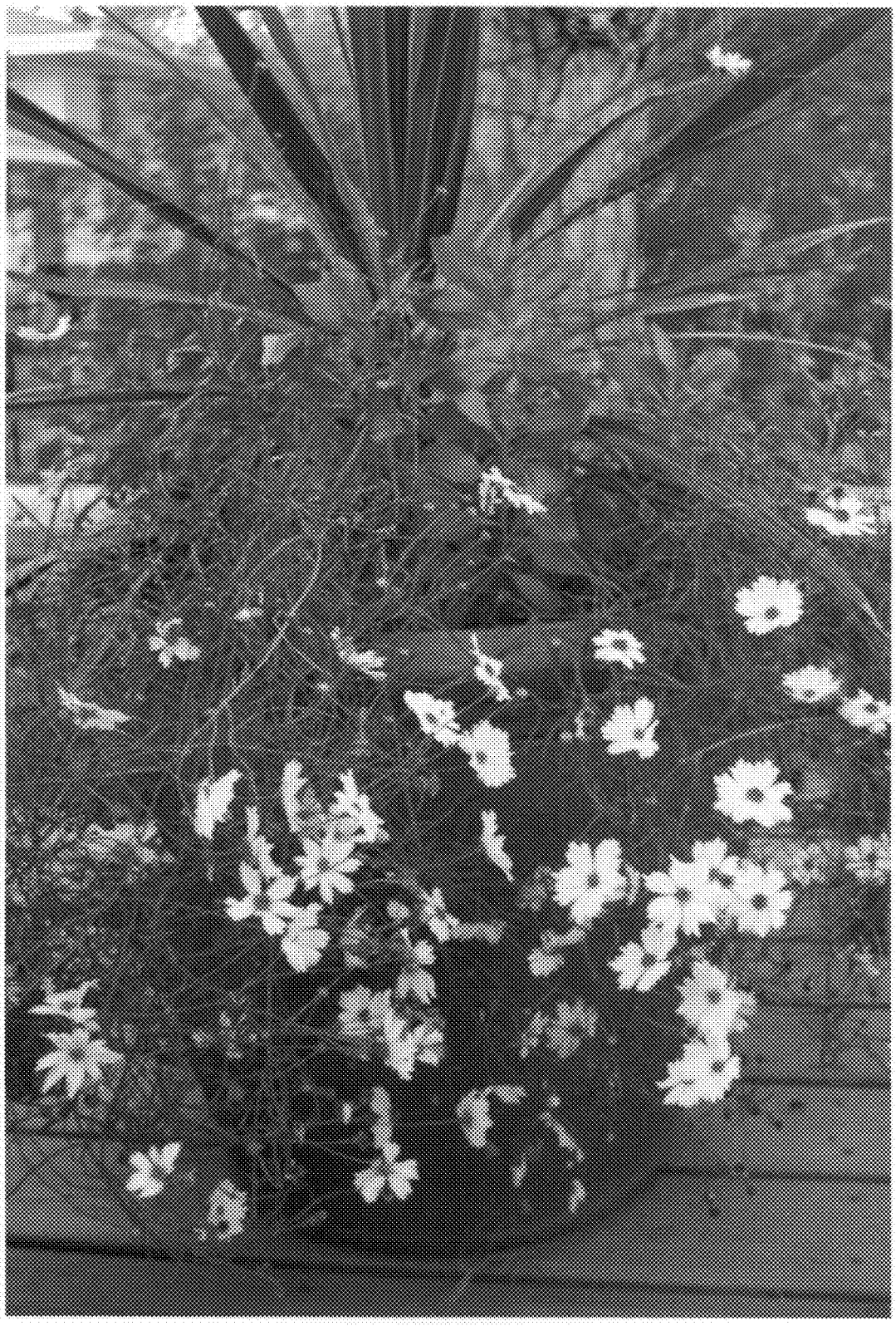
Figure 2:
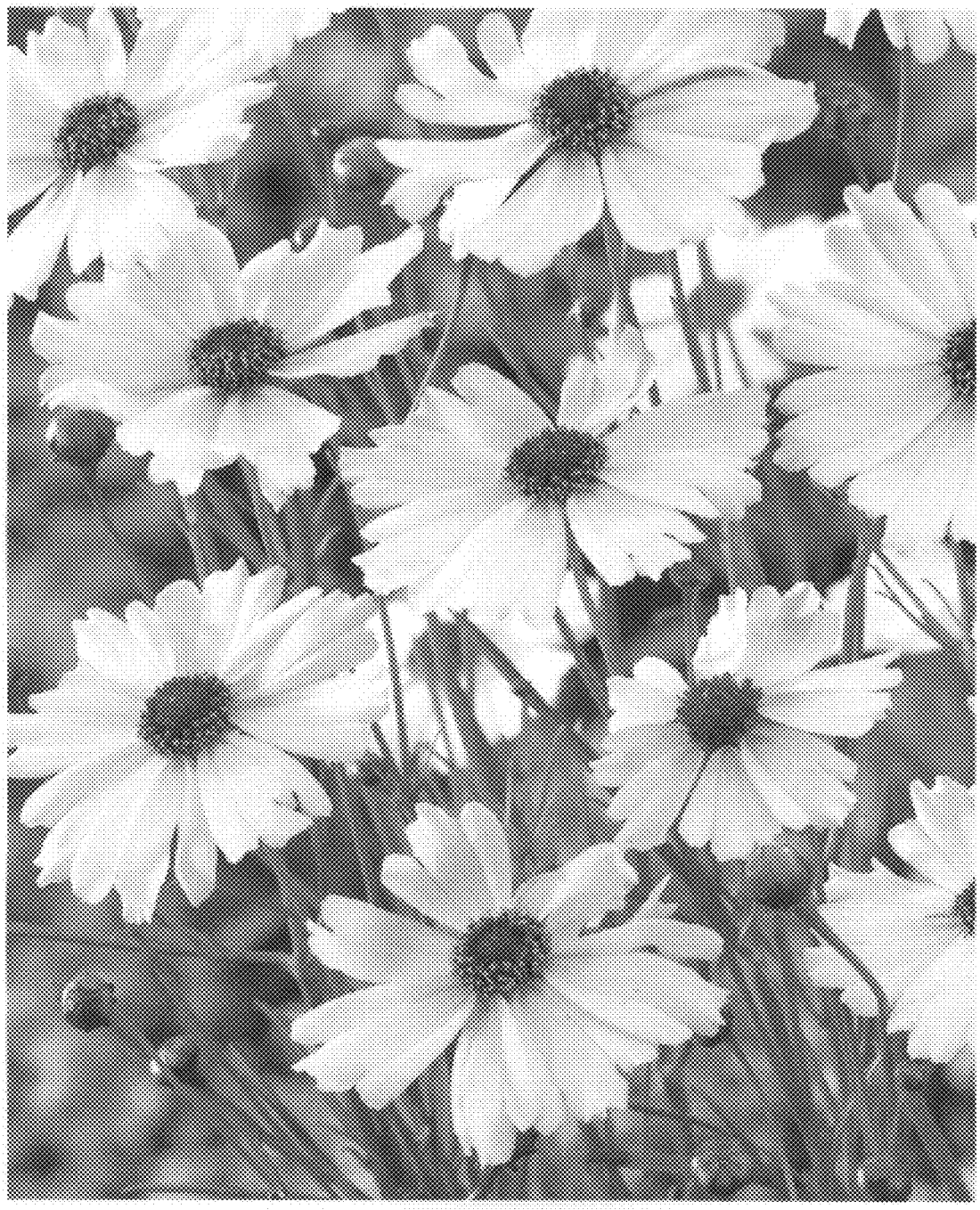

The photograph in FIG. 2 was taken in late summer of a six month-old plant of 'Limbo' as grown outdoors in a two-gallon container in The Netherlands and provides a close-up view of inflorescences of 'Limbo'.

The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for three growing seasons in a trial garden in Hubbardston, Mass. with the detailed botanical data collected from five month-old plants of the new cultivar as grown in two-gallon containers in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from June through August in central Massachusetts.

*Plant habit.*—Herbaceous annual, well-branched to produce a bushy habit.

*Height and spread.*—Reaches 16 to 24 inches (40.6 to 61 cm) in height and 24 inches (61 cm in width) in 3 months from a rooted cutting.

*Cold hardiness.*—Has not been tested as it is grown as an annual.

*Diseases resistance.*—No particular resistance or susceptibility has been observed.

*Root description.*—Fibrous, fine and well-branched.

Growth and propagation:

*Propagation.*—Terminal stem cuttings.

*Growth rate.*—Vigorous.

Stem description:

*Shape.*—Oval, solid.

*Stem color.*—137A.

*Stem size.*—Main stem averages 48 cm in length and 3.5 mm in width with laterals variable in length with an average of 16 cm in length (excluding peduncles) and 2 mm in width.

*Stem surface.*—Very finely puberulent when young, ridged and finely puberulent when mature.

*Branching habit.*—Numerous basal branches (an average of 12 per one year-old plant) with an average of 9 secondary branches emerging opposite at a nodes, internode length an average of 8 cm.

Foliage description:

*Leaf division.*—Simple.

*Leaf margins.*—Ranges from entire, to tri-fid to 5 lobed (deeply divided).

*Leaf size.*—Variable, entire leaves; up to 6.5 cm in length and 4 mm in width, tri-fid leaves; up to 7 cm in length and 6 cm in width with center lobe an average of 6 mm in length and 3 mm in width and secondary lobes an average of 2 cm in length and 2 mm in width, 5-lobed; up 7 cm in width and 6 cm in width when mature with center lobe an average of 7 mm in length and 4 mm in width and secondary lobes an average of 4 cm in length and 3 mm in width.

*Leaf shape.*—Leaves and leaf lobes; very narrowly oblanceolate to linear.

*Leaf base.*—Attenuate.

*Leaf apex.*—Acute.

*Leaf venation.*—Pinnate, not conspicuous, coloration same as leaf on both surfaces.

*Leaf attachment.*—Sessile.

*Leaf arrangement.*—Opposite.

*Leaf surface.*—Dull and very finely puberulent on upper surface and lower surface.

*Leaf color.*—Young and mature upper surface; N137A, young and mature lower surface; N137B.

Inflorescence description:

*Inflorescence type.*—Composite with ray florets surrounding disk florets in the center, forming a radiant head, inflorescences are borne on terminals of lateral branches on thin peduncles.

*Lastingness of inflorescence.*—About one week until senescence of ray florets, bracts and disk florets are persistent.

*Fragrance.*—None detected.

*Quantity of inflorescences.*—An average of 4 per lateral branch, an average of 100 per plant grown in a one-gallon container at one time, new inflorescences are continuously produced throughout the growing season.

*Inflorescence size.*—Up to 1 cm in depth and up to 4 cm in diameter with disk portion up to 8 mm in diameter.

*Inflorescence buds.*—Average of 6 mm in depth and diameter, shape is spherical, color is N25C with base of inner bracts 147A in color, apex becomes 8D in color just prior to opening.

*Peduncle.*—Strong, thin, average of 7.5 cm in length and 1 mm in diameter, a blend of 137A in color, surface is finely puberulent with fine ridges.

*Pedicels.*—None.

Involucral bracts:

*Bract number.*—8 outer bracts arranged in 2 rows, about 8 inner bracts arranged in 2 rows.

*Bract arrangement.*—Outer bracts are fused into cone-shaped base about 4 mm in length and 3 mm width with free apex of each held slightly upward, inner bracts surround receptacle with a campanulate form with apical portion un-fused, spreading, and held close to ray florets.

*Bract size.*—Outer bracts; free portion an average of 2 mm in length and width, inner bracts; up to 9 mm in length and 3.5 mm in width with free portion an average of 5 mm in length and 3 mm in width.

*Bract color.*—Outer bracts; 137A on both surfaces with thin margins 145D, inner bracts; fused portion 147A, un-fused portion N25C.

*Bract texture.*—Waxy on outer and inner bracts.

*Bract apex.*—Acute on outer and inner bracts.

*Bract base.*—Truncate on outer and inner bracts.

*Bract margins.*—Entire on outer and inner bracts.

*Bract shape.*—Outer bracts; free portion ovate, inner bracts; free portion broadly lanceolate.

Ray florets (sterile):

*Number.*—8.

*Shape.*—Obovate, appearance of three longitudinal sections with center section slightly longer and apex of each free.

*Size.*—An average of 1.7 cm in length and 1.1 cm in width.

*Apex.*—3-lobed with center lobe slightly emarginate and side lobes rounded.

*Base.*—Broadly cuneate.

*Margins.*—Entire on sides, lobed at apex.

*Aspect.*—Held slightly cupped upward when opening and becoming nearly horizontal.

*Texture.*—Glabrous on upper and lower surfaces.

*Color.*—Upper surface when opening and mature; NN155A and suffused near base with 4A, lower surface when opening and mature; NN155A and suffused on lower one-half with 1B.

Disk florets (perfect):

*Shape.*—Tubular, corolla is fused, flared at apex.

*Size.*—About 4 mm in length and 0.8 mm in width.

*Color.*—In masse; a blend of 166A and 25A when fully open and becoming 200A when dried and ray florets drop, corolla; base (tube) is 21B, flared portion is 25A and translucent.

*Number.*—Numerous, about 100.

*Receptacle.*—About 3 mm in diameter and 2 mm in depth, 147C in color.

Reproductive organs:

*Presence.*—Disk florets are perfect, ray florets are sterile.

*Gynoecium.*—1 Pistil, 5 mm in length, style is very fine and about 20B in color and translucent, bifid pilose stigma is 25A in color and about 1 cm in width when strongly recurved, ovary is oblong in shape, 1.5 mm in length, 1 mm in width, inferior, and 145D in color.

*Androcoecium.*—5 stamens, fused into tube surrounding style, 1.5 mm in length and 0.5 mm in width, about 200A in color, pollen appears sparse in quantity and about 15A in color.

*Fruit/seed.*—Sterile.

It is claimed:

1. A new and distinct cultivar of *Coreopsis* plant named 'Limbo' as herein illustrated and described.

* * * * *